US00PP27777P3

(12) United States Plant Patent
Gmitter, Jr.

(10) Patent No.: US PP27,777 P3
(45) Date of Patent: Mar. 14, 2017

(54) SWEET ORANGE TREE NAMED 'UF 11-1-24'

(50) Latin Name: *Citrus sinensis*
Varietal Denomination: UF 11-1-24

(71) Applicant: Florida Foundation Seed Producers, Inc., Marianna, FL (US)

(72) Inventor: Frederick G. Gmitter, Jr., Lakeland, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 59 days.

(21) Appl. No.: 14/544,743

(22) Filed: Feb. 10, 2015

(65) Prior Publication Data

US 2016/0234988 P1 Aug. 11, 2016

(51) Int. Cl.
*A01H 5/08* (2006.01)

(52) U.S. Cl.
USPC ..... Plt./202

(58) Field of Classification Search
USPC ..... Plt./156, 201, 202
See application file for complete search history.

(56) References Cited

U.S. PATENT DOCUMENTS

2015/0052645 P1 2/2015 Grosser

OTHER PUBLICATIONS

UF-IFAS, University of Florida; "New sweet orange cultivars", http://research.ifas.ufl.edu/docs/pdf/publications/CitrusInsert.sm.pdf, 2 pages.*
U.S. Appl. No. 14/121,859, filed Oct. 27, 2014, Grosser.
U.S. Appl. No. 14/121,945, filed Nov. 5, 2014, Grosser.
U.S. Appl. No. 14/121,946, filed Nov. 5, 2014, Grosser.

* cited by examiner

*Primary Examiner* — Susan McCormick Ewoldt
*Assistant Examiner* — Karen Redden
(74) *Attorney, Agent, or Firm* — Dentons US LLP

(57) ABSTRACT

'UF 11-1-24' is a new and distinct, nearly seedless, midseason sweet orange. Trees of 'UF 11-1-24' produce fruit that have higher soluble solids/box ratio, and juice color than 'Midsweet' orange, the industry standard mid-season sweet orange cultivar. Fruit of 'UF 11-1-24' also reach a higher solids/acidity ratio than any other 'Midsweet' clones, enabling a slightly earlier harvest, and thus, potentially avoiding freezing events common in late December/early January harvests.

6 Drawing Sheets

Latin name of the genus and species of the plant claimed: *Citrus sinensis*.

Variety denomination: 'UF 11-1-24'.

BACKGROUND OF THE INVENTION

'UF 11-1-24' is a new and distinct, nearly seedless, midseason sweet orange with higher soluble solids/box ratio, and juice color than the current industry standard, 'Midsweet'. 'UF 11-1-24' arose as a single tree from among more than 100 trees produced in 1991 by irradiation of budwood of the sweet orange cultivar 'Midsweet', released by the USDA in 1987. These trees were planted in 1992 and grown near Venus, Fla. The original tree of 'UF 11-1-24' was selected after several seasons of evaluation on the basis of producing low-seeded and seedless fruit, whereas the original variety, 'Midsweet', typically produces between 10-15 seeds per fruit. Trees of 'UF 11-1-24' were asexually propagated by budding onto commercial rootstocks, along with several other low-seeded selections made from the original planting; together these were grown in a replicated field trial in north central Florida. All of those trees are true-to-type. 'UF 11-1-24' was identified as the best performer in the trial. The individual source tree from which budwood was collected for phytosanitary cleanup was chosen on the basis of its superior performance relative to the other individual trees of 'UF 11-1-24'. It consistently yielded more fruit, with higher soluble solids than the selection mean value.

SUMMARY OF THE INVENTION

'UF 11-1-24' produces fruit that resembles ordinary 'Midsweet' oranges. However, the number of seeds per fruit is dramatically reduced, ranging typically between 0 and 4. 'Midsweet' is grown for mid-season juice processing, though some of the fruit has also been marketed fresh. The low seed numbers make 'UF 11-1-24' more desirable as a fresh fruit option, while retaining the qualities that have made 'Midsweet' formerly the third most widely planted sweet orange in Florida, following 'Valencia' and 'Hamlin'. 'UF 11-1-24' was chosen from among the various seedless selections trialed because of its consistently higher Brix and pounds solids/box (FIGS. 1 and 2, respectively). In addition, 'UF 11-1-24' also reaches higher soluble solids/acidity ratios (averaging 19.4 vs. 17.1, the second best line in this planting) than any of the other 'Midsweet' clones, enabling a slightly earlier harvest that may avoid freezing events common in late December and early January. Finally, the average juice color score for 'UF 11-1-24' across the five years of testing was 35.3, a full point higher than any of the other selections in the trial.

For the 2011-2012 season, the average number of 90-lb boxes of 'UF 11-1-24' fruit produced (the standard measure of sweet orange productivity in Florida) was 4.32 boxes/tree, or 388.13 lbs fruit/tree for trees grown on Carrizo (unpatented) citrange rootstock. In the 2011-12 season, the tree from which budwood was collected and selected as the source for claimed variety 'UF 11-1-24' produced 4.86 boxes, or 437.4 lbs fruit/tree.

Fruit of the claimed variety were routinely stored after harvest for up to 2 weeks at 4-6° C. before being sampled for juice quality determinations, every season. Fruit of 'UF 11-1-24' displayed no evidence of fruit decay in that period of time, similar to other samples of many other sweet orange selections harvested at the same time and held under identical conditions.

BRIEF DESCRIPTION OF THE DRAWINGS

'UF 11-1-24' is illustrated by the accompanying photographs, which show the tree's form, foliage, and fruit. The colors shown are as true as can be reasonably obtained by conventional photographic procedures. The photographs are of a tree approximately 16 years old.

DETAILED BOTANICAL DESCRIPTION

Figure 1:
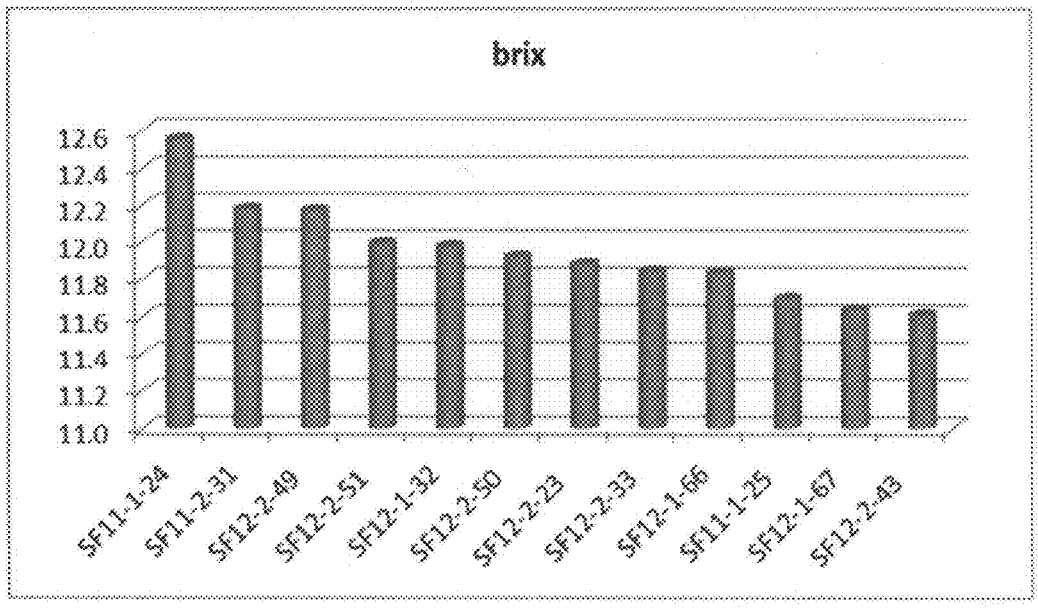
FIG. 1—Shows Brix levels across five seasons (2007-2011). Fruit harvest dates varied from year to year, based on availability of commercial harvesting crews, but they were always sometime in the month of January.
Figure 2:
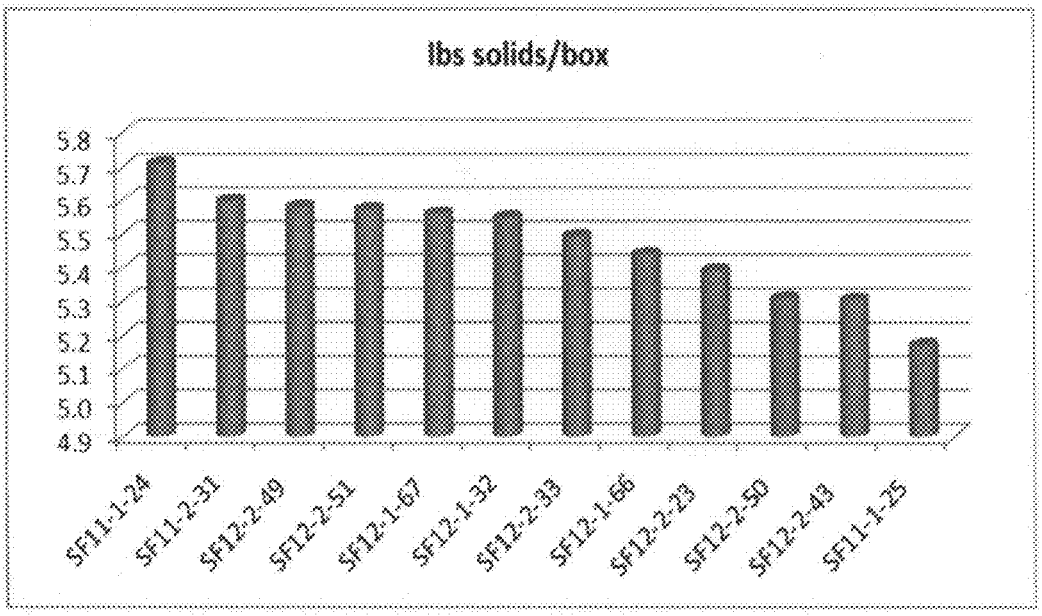
FIG. 2—Shows mean pounds solids/box across five seasons (2007-2011). Fruit harvest dates varied from year to year, based on availability of commercial harvesting crews, but they were always sometime in the month of January.
Figure 3:
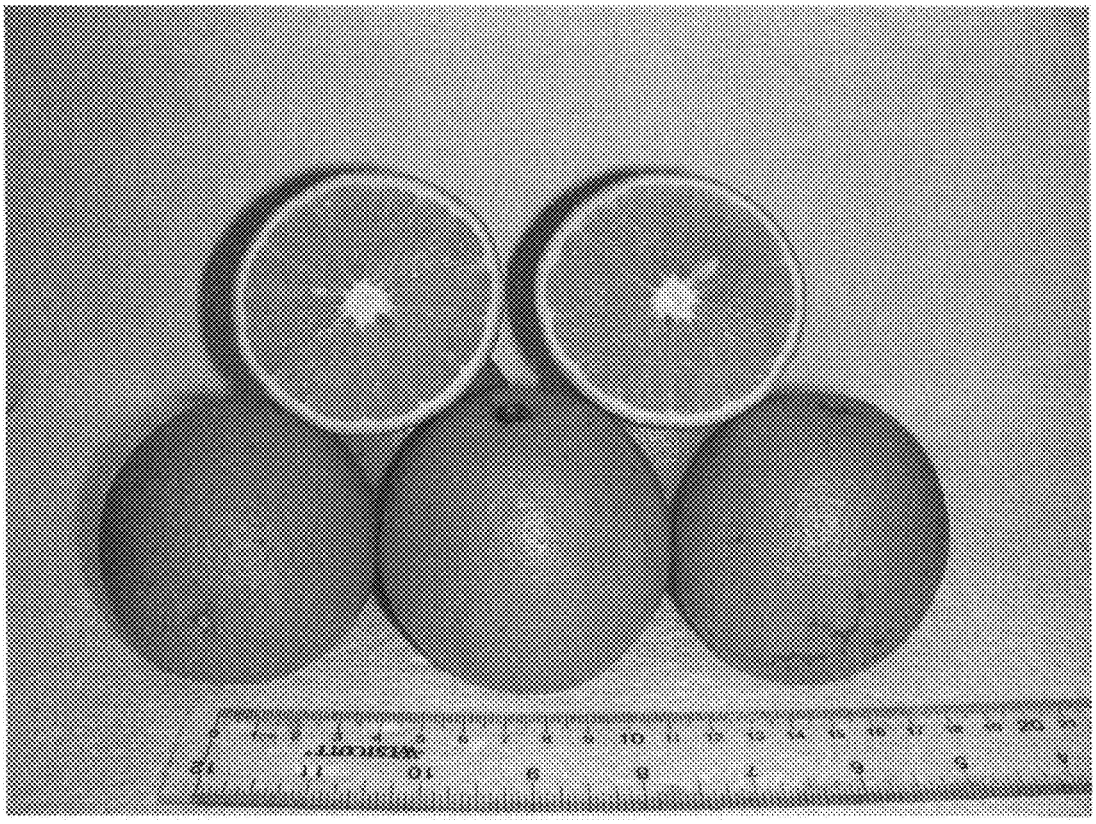
FIG. 3—Shows typical size, shape, color, and low number of seeds of fruit.
Figure 4:
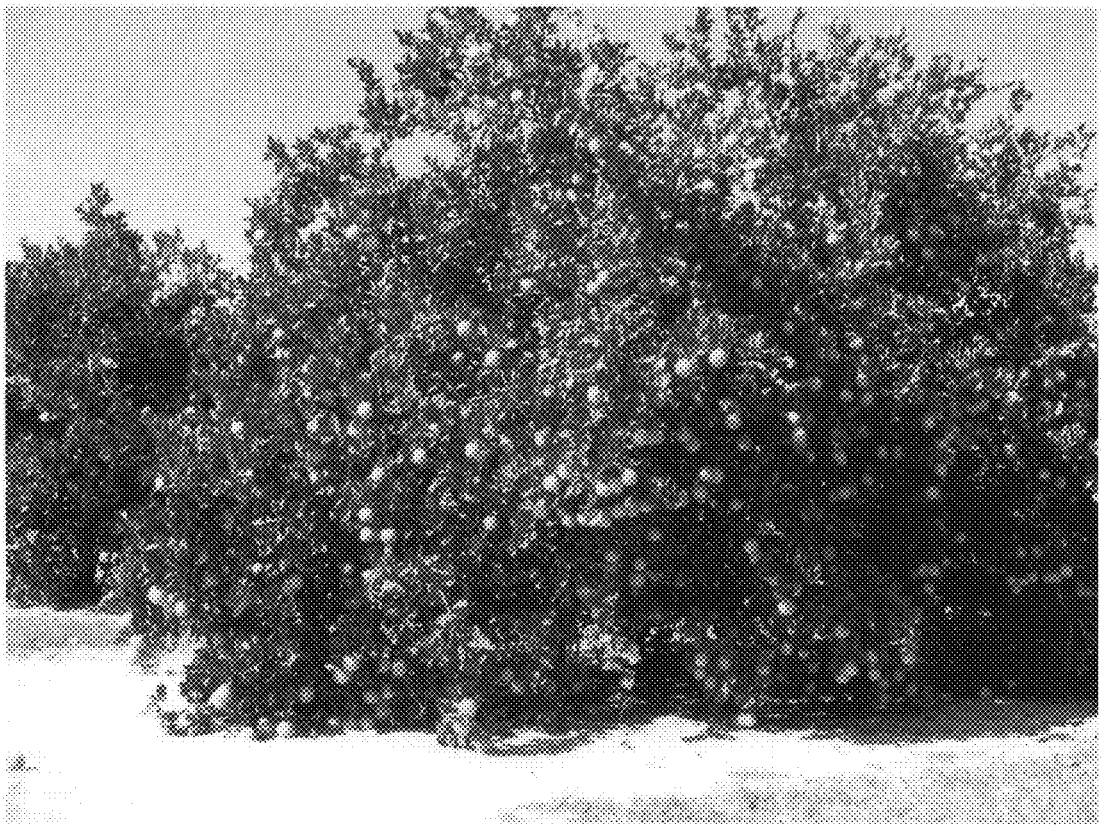
FIG. 4—Shows typical tree growth and bearing habit.
Figure 5:
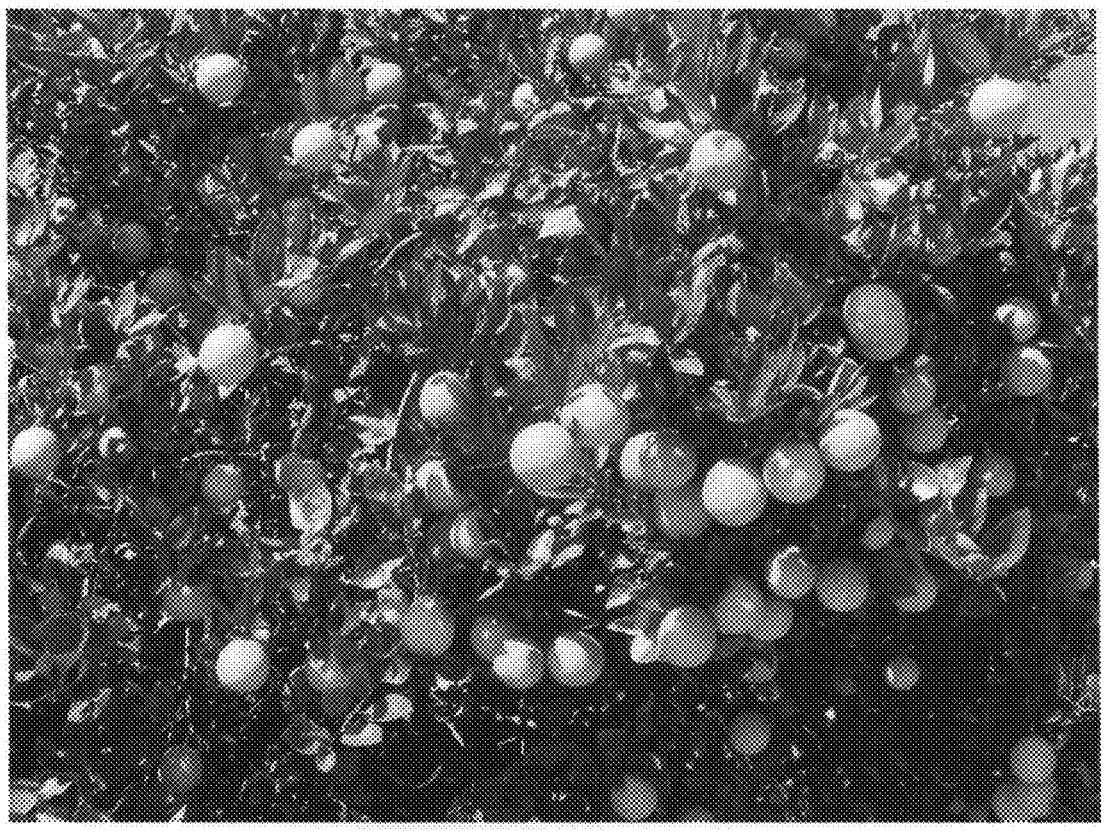
FIG. 5—Shows a close view of typical fruiting habit of the source tree of 'UF 11-1-24' at maturity, January 2012.
Figure 6:
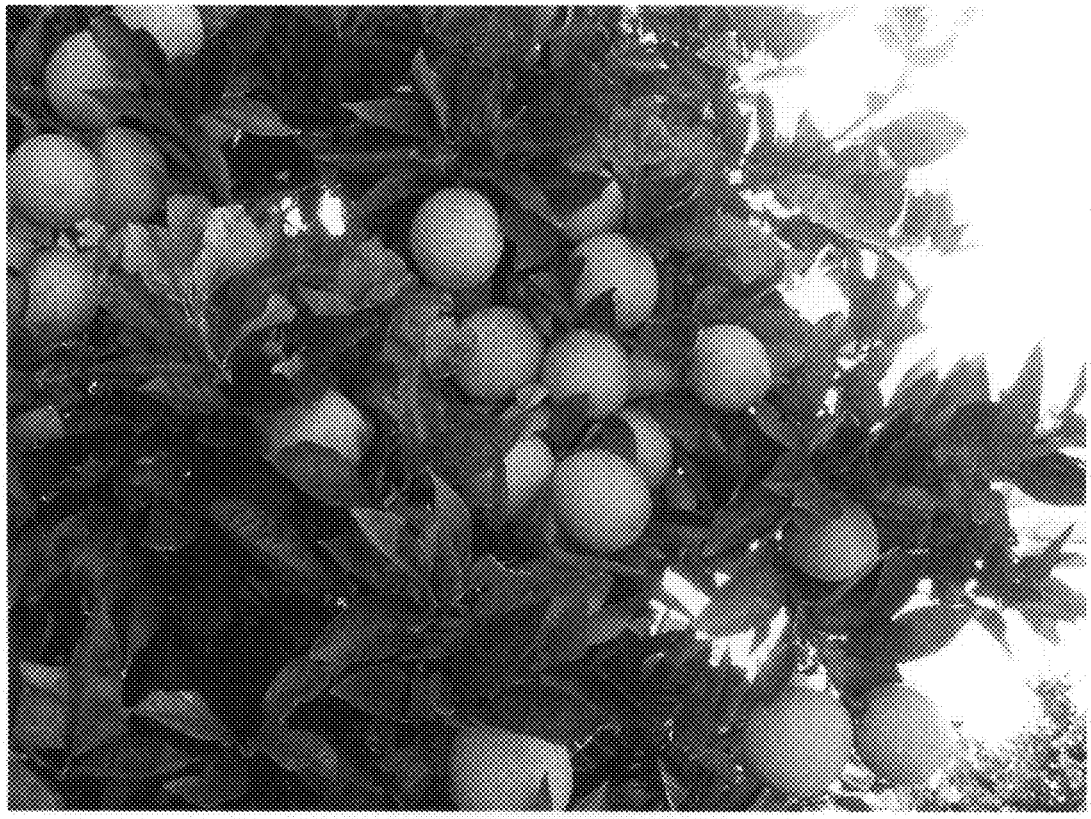
FIG. 6—Shows a closer view of fruit and foliage characteristics of the source tree of 'UF 11-1-24' at maturity, January 2012.

Phenotypic Description of *Citrus sinensis* 'UF 11-1-24'

The following detailed description sets forth the distinctive characteristics of 'UF 11-1-24'. The present botanical description is that of the variety grown on 10-year-old trees growing on 'Carrizo' citrange rootstock (*C. sinensis*×*Poncirus trifoliata*) in north central Florida. The colors (except those in common terms) are described from The R.H.S. Colour Chart published by The Royal Horticultural Society in London (second edition), in association with the Flower Council of Holland.

Classification:

*Botanical.*—*Citrus sinensis.*

*Common name.*—Sweet orange.

Parentage: 'UF 11-1-24' was selected as a bud sport mutation induced by irradiation of 'Midsweet' (unpatented) sweet orange budwood.

Tree:

*Ploidy.*—Diploid.

*Size.*—Large.

*Tree height.*—4.27 to 4.4 m.

*Tree spread.*—4.0 to 4.6 m.

*Vigor.*—Very vigorous.

*Density.*—Canopies are very dense.

*Form.*—The tree is obloid shaped with both lateral and upright branches growing; branches with fruit exhibit drooping.

*Growth habit.*—Both upright and lateral growth with low medium angle.

Trunk:

*Trunk diameter.*—17.8 to 18 cm in diameter at 30 cm above the ground, 16 year old tree.

*Trunk texture.*—Smooth.

*Trunk bark color.*—RHS 197A (grey-green); irregularly striated with RHS N189B (greyed-green) and RHS 189A (greyed-green).

Branches:

*Crotch angle.*—First crotch forms a 35 to 40-degree angle, middle crotch forms a 40-degree angle.

*Branch length.*—Branches reach 4.5 meters from the first crotch to the tip of the branch.

*Branch texture.*—Relatively smooth, occasionally with small thorns or spines.

*Branch color* (*shoots from previous flush, hardened, and* 4 *to* 5 mm *in diameter*).—RHS 137B (green).

Leaves:

*Size* (*lamina average*).—Length: 94 mm. Width: 41 mm. L/W ratio: 2.1 to 2.3.

*Thickness.*—Regular and average compared to commercial sweet oranges.

*Type.*—Simple.

*Arrangement.*—Alternate.

*Shape.*—Elliptical.

*Apex.*—Very slightly retuse.

*Base.*—Acute to sub-obtuse.

*Margin.*—Entire and slightly undulate.

*Surface.*—Upper surface: Glabrous. Lower surface: Medium veins that are pinnately netted.

*Color.*—Upper surface (adaxial): RHS 137A (green). Lower surface (abaxial): RHS 138B (green).

*Petiole.*—Shape: Brevipetiolate (shorter than leaf lamina); the junction between petiole and lamina is articulate. Width (petiole wing): Narrow. Shape (petiole wing): Obovate. Length: 10-12 mm. Width: 2 to 3 mm. Color: RHS 137A (green).

Flowers and flower buds:

*Type.*—Hermaphrodite.

*Bearing.*—Flowers grow from leaf axillaries and leaf terminals; 2-5 or more flowers grow in a cluster, most single flowers grow from leaf axillaries; each flower branch consists of 3 to 4 flower clusters.

*Flower diameter.*—Fully opened flowers have an average diameter of 31.5 to 31.6 mm.

*Flower depth.*—Typical flower has an average depth of 14.8 mm.

*Blooming period.*—First bloom: Observed in early March 2011, central Florida. Full bloom: Observed in mid-March 2011, central Florida.

*Flower bud size.*—Length: Initial visible flower bud is 3.3 mm in length. Diameter: Initial visible flower bud is 3.0 mm in diameter; mature flower bud before opening is 8.4 to 9.0 mm in diameter.

*Flower bud shape.*—Initial visible flower bud has a round ball shape; mature flower bud has an elongated olive shape.

*Flower bud color.*—Initial bud: RHS 142B (green). Mature flower bud: RHSNN155C (white) with RHS 154D (yellow-green) spots distributed at tip of the flower bud.

*Flower petals*.—Number: 5. Length: 20.5 mm. Width: 6.5 mm. Shape: Flat, spatula shaped. Apex shape: Smooth, acute shaped. Base shape: Even obtuse.

*Color*.—Upper surface: RHSNN155C (white). Lower surface: RHSNN 155C (white) with RHS 154D (yellow-green) spots distributed toward the petal apex. Margin: Smooth.

*Sepal*.—Number (per flower): 5 per flower. Shape: Delta shaped with an acute angle at the apex. Length: 3.5 mm. Width: 3.5 mm. Apex shape: Delta with acute angle. Margin: Smooth.

*Color*.—Upper surface: RHS 149C (yellow-green). Lower surface: RHS 149C (yellow-green).

*Fragrance*.—Fragrant.

*Pedicel*.—Number: 1. Length: 9.2 mm. Diameter: 1.5 mm. Color: RHS 143C (green).

*Reproductive organs*.—Fertility: Self-fertile. Stamen length: 11.5 to 11.7 mm. Anther. Length: 3.2 mm. Width: 1.0 to 1.1 mm. Color: RHS 13C (yellow). Filament length: 8.8 to 9.2 mm. Pollen amount: Abundant. Pollen color (general): RHS 13A (yellow).

*Pistil*.—Number: 1. Length: 8.0 to 9.0 mm. Color: RHS 144D (yellow-green).

*Style length*.—6.0 mm.

*Style diameter*.—1.1 to 1.2 mm.

*Style color*.—RHS 143D (green).

*Ovary shape*.—Oval shaped.

*Ovary diameter*.—2.6 mm.

*Ovary color*.—RHS 143C (green).

Fruit:

*Size*.—Uniform.

*Width*.—65 to 74 mm on average.

*Length*.—64 to 74 mm on average.

*Average weight* (*per individual fruit*).—170 to 180 g.

*Shape*.—Round and earth shaped.

*Shape* (*cross-section*).—Round.

*Apex*.—Truncated.

*Apex cavity diameter*.—N/A.

*Base*.—Smooth.

*Base cavity diameter*.—2.0 to 2.2 mm.

*Harvesting*.—First pick around late January (based on season and rootstock); last pick around mid-March, although fruit continue to hold on the tree for a longer time (based on season and rootstock).

*Fruit stem* (*short stem connecting the fruit*).—Length: 13 to 13.8 mm. Diameter: 3.5 to 4.0 mm. Color: RHS 197 (greyed-green) with RHS 137 (green) strip.

Skin:

*Adherence*.—Adherence between albedo (mesocarp) and flesh (endocarp) is strong, not easy to peel compared to 'Navel' sweet orange.

*Thickness*.—3.0 to 4.0 mm on average.

*Texture*.—Slightly pebbled.

*Color*.—Flavedo (epicarp): Ranges between RHS 20B (yellow-orange) to RHS 20A (yellow-orange). Albedo (mesocarp): RHS 10D (yellow). Stylar end: Closed.

*Rind oil cell density*.—196 to 200 oil cells/square cm.

Flesh:

*Number of segments*.—Average of 11 or 12 segments per fruit.

*Segment walls*.—Medium soft with sufficient strength to maintain integrity as separated.

*Juice*.—Abundant.

*Color*.—Uniformly RHS 20B (yellow-orange).

*Texture*.—Soft.

*Vesicles*.—Length: Ranges from 9.0 to 13 mm on average. Diameter (thickness): 1.0 to 2.0 mm on average.

*Eating quality* (*varies from season to season*).—Soluble solids (average): 12.8 Brix. Acidity (average): 0.65%. Sugar Acid Ratio: 19.7.

Seeds:

*Type*.—Polyembryonic.

*Number*.—Ranges from 0 to 4.

*Shape*.—Seed shapes are not uniform, clavate to semi-deltoid shaped.

*Size*.—Length: 13 to 14 mm. Width: 6.0 to 6.8 mm.

*Seed coat color*.—Outer Surface: RHS NN155A (white) and slightly wrinkled. Inner surface: RHS 165B (greyed-orange).

*Cotyledon color*.—RHS 155C (white).

Resistance to disease: No obvious disease problems have been observed in the trees or fruit currently grown, but systematic resistance testing has not been yet conducted.

What is claimed is:

1. A new and distinct cultivar of sweet orange tree as illustrated and described herein.

* * * * *